United States Patent [19]

Middleton

[11] 3,965,074

[45] June 22, 1976

[54] HOMOPOLYMERS OF POLYFLUORINATED VINYL ISOCYANATES

[75] Inventor: William J. Middleton, Chadds Ford, Pa.

[73] Assignee: E. I. Du Pont de Nemours and Company, Wilmington, Del.

[22] Filed: Oct. 22, 1975

[21] Appl. No.: 624,975

Related U.S. Application Data

[62] Division of Ser. No. 435,494, Jan. 22, 1974, which is a division of Ser. No. 176,709, Aug. 31, 1971, Pat. No. 3,816,495.

[52] U.S. Cl. ............................. 260/77.5 R; 252/8.6; 260/77.5 CR; 526/242; 526/248; 526/249; 427/390; 427/391
[51] Int. Cl.$^2$ ............................................. C08G 18/81
[58] Field of Search .................. 260/77.5 R, 453 AL

[56] References Cited
UNITED STATES PATENTS

| | | | |
|---|---|---|---|
| 3,242,140 | 3/1966 | Hoover | 260/77.5 |
| 3,468,923 | 9/1969 | Koenig et al. | 260/453 |

*Primary Examiner*—Lewis Gotts
*Assistant Examiner*—Dolph H. Torrence

[57] ABSTRACT

Disclosed herein are polyhalogenated isocyanates (intermediates for polyfluorinated vinyl isocyanates); polyfluorinated vinyl isocyanates, process therefor, and homopolymers and copolymers thereof; and use of said polyfluorinated vinyl isocyanate homopolymers and copolymers as water and oil repelling agents for cloth and paper.

3 Claims, No Drawings

HOMOPOLYMERS OF POLYFLUORINATED VINYL ISOCYANATES

CROSS-REFERENCE TO RELATED APPLICATIONS

This is a division of application Ser. No. 435,494, filed Jan. 22, 1974 which in turn is a division of Ser. No. 176,709, filed Aug. 31, 1971, now, U.S. Pat. No. 3,816,,495.

BACKGROUND OF THE INVENTION

1. Field of the Invention

This invention relates to novel halogen-containing isocyanates, to their preparation and to their use.

2. Description of the Prior Art

Reaction of benzophenone imine and oxalyl chloride to produce chloro(diphenyl)methyl isocyanate is reported by Samarai et at., Chem. Abs. 69, 2681w (1968). The preparation of perfluoroalkly isocyanates by the reaction of perfluoroacyl chlorides with sodium azide has been reported by A. H. Ahlbrecht in U.S. Pat. No. 2,617,817 (1952). The removal of of chlorine from a 1,2-dichloro fluoroaliphatic compound by means of zinc to from the corresponding fluoroolefinic compound is known; see Hudlicky, "Chemistry of Organic Fluorine Compounds," the MacMillan Company, New York, 1962, pp. 263–269.

SUMMARY AND DETAILS OF THE INVENTION PRODUCT

The novel polyhalogenated isocyanates of this invention have the generic formula $$XCF_2-\underset{\underset{Y}{|}}{\overset{\overset{R}{|}}{C}}-N=C=O$$

wherein:
R is fluorine, lower perfluoroalkyl, lower ω-chloroperfluoroalkyl or lower ω-hydroperfluoroalkyl,
X and Y are each fluorine, chlorine or bromine with the proviso that only one of X and Y is fluorine.

Representative isocyanates of this invention are given in Table 1 below.

TABLE 1

| | Name | Structure |
|---|---|---|
| (1) | 1,2-dichloro-2,2-difluoro-1-(trifluoromethyl)ethyl isocyanate | $CF_3-\underset{\underset{Cl}{|}}{\overset{\overset{CF_2Cl}{|}}{C}}-N=C=O$ |
| (2) | 1,2-dichloro-1,2,2-trifluoroethyl isocyanate | $F-\underset{\underset{Cl}{|}}{\overset{\overset{CF_2Cl}{|}}{C}}-N=C=O$ |
| (3) | 1-chloro-2,2,2-trifluoro-1-(trifluoromethyl)ethyl isocyanate | $Cl-\underset{\underset{CF_3}{|}}{\overset{\overset{CF_3}{|}}{C}}-N=C=O$ |
| (4) | 1,2-dichloro-2,2-difluoro-1-(chlorodifluoromethyl)ethyl isocyanate | $Cl-\underset{\underset{CF_2Cl}{|}}{\overset{\overset{CF_2Cl}{|}}{C}}-N=C=O$ |
| (5) | 1-chloro-1-(trifluoromethyl) pentafluoropropyl isocyanate | $CF_3CF_2-\underset{\underset{Cl}{|}}{\overset{\overset{CF_3}{|}}{C}}-N=C=O$ |
| (6) | 1,3-dichloro-1-(trifluoromethyl)tetrafluoropropyl isocyanate | $ClCF_2CF_2-\underset{\underset{Cl}{|}}{\overset{\overset{CF_3}{|}}{C}}-N=C=O$ |
| (7) | 1-chloro-3H-1-(trifluoromethyl)tetrafluoropropyl isocyanate | $HCF_2CF_2-\underset{\underset{Cl}{|}}{\overset{\overset{CF_3}{|}}{C}}-N=C=O$ |
| (8) | 2-chloro-1,1,2,2-tetrafluoroethyl isocyanate | $ClCF_2CF_2-N=C=O$ |
| (9) | 1,2-dibromo-1,2,2-trifluoroethyl isocyanate | $BrCF_2-\underset{\underset{Br}{|}}{C}F-N=C=O$ |
| (10) | 2-bromo-1-chloro-1,2,2-trifluoroethyl isocyanate | $BrCF_2-\underset{\underset{Cl}{|}}{C}F-N=C=O$ |
| (11) | 2-bromo-1,1,2,2-tetrafluoroethyl isocyanate | $BrCF_2CF_2-N=C=O$ |

The novel polyfluorinated vinyl isocyanates of this invention have the generic formula $$CF_2=\overset{\overset{R}{|}}{C}-N=C=O$$

wherein:
R is fluorine, lower perfluoroalkyl, lower ω-chloroperfluoroalkyl or lower ω-hydroperfluoroalkyl.

Representative vinyl isocyanates of this invention are given in Table 2 below.

TABLE 2

| | Name | Structure |
|---|---|---|
| (1) | 2,2-difluoro-1-(trifluoromethyl)vinyl isocyanate | $CF_2=\overset{\overset{CF_3}{|}}{C}-N=C=O$ |
| (2) | trifluorovinyl isocyanate (perfluorovinyl isocyanate) | $CF_2=\overset{\overset{F}{|}}{C}-N=C=O$ |
| (3) | 2,2-difluoro-1-(chlorodifluoromethyl)vinyl isocyanate | $CF_2=\overset{\overset{CF_2Cl}{|}}{C}-N=C=O$ |
| (4) | 2,2-difluoro-1-(pentafluoroethyl)vinyl isocyanate | $CF_2=\overset{\overset{C_2F_5}{|}}{C}-N=C=O$ |
| (5) | 2,2-difluoro-1-(2-chlorotetrafluoroethyl)vinyl isocyanate | $CF_2=\overset{\overset{CF_2}{|}\overset{|}{CF_2Cl}}{C}-N=C=O$ |
| (6) | 2,2-difluoro-1-(2H-tetrafluoroethyl)vinyl isocyanate | $CF_2=\overset{\overset{CF_2}{|}\overset{|}{CF_2H}}{C}-N=C=O$ |

Included within the scope of this invention are the novel homopolymers of the fluorinated vinyl isocyanates of Table 2. Also included are copolymers (terpolymers, etc.) containing the polyfluorinated vinyl isocyanate polymer units therein.

Copolymers may be comprised solely of fluorine-containing copolymers, or, non-fluorine containing copolymers copolymerized with the florinated vinyl isocyanates of this invention. Representative copolymers include tetrafluoroethylene/1,1-difluoro-2-(trifluoromethyl)vinyl isocyanate, trifluorovinyl isocyanate/perfluoro(2-methylene-4-methyl-1,3-dioxolane), trifluorovinyl isocyanate/vinylidene fluoride/perfluoro(2-methylene-4-methyl-1,3-dioxolane), and 1,1-difluoro-2-(trifluoromethyl)vinyl isocyanate/vinylidene fluoride/perfluoro(2-methylene-4-methyl-1,3-dioxolane).

Novel homopolymers, and novel copolymers of the vinyl isocyanate with fluoroolefins, can be prepared by standard techniques including initiation by free radicals and/or anions. Preferred copolymers are those derived by copolymerization with fluorine-containing comonomers, such as vinyl fluoride, vinylidene fluoride, trifluoroethylene, chlorotrifluoroethylene, tetrafluoroethylene, hexafluoropropylene, trifluoromethyl trifluorovinyl ether, and perfluoro(2-methylene-4-methyl-1,3-dioxolane).

The homopolyer is readily soluble in solvents ordinarily used with vinyl polymers, such as acetone, chloroform, and the like. The most preferred copolymer (with tetrafluoroethylene) is not readily soluble in ordinary solvents. Both the homopolymer and the tetrafluoroethylene copolymer are repellant toward water or mineral oil, and can be applied to cloth and to paper to give these materials water and oil repelling qualities.

Because of the presence of isocyanate groups, the polymers are also reactive with compounds containing hydroxyl or amino groups and can be crosslinked through reaction with molecules containing more than one of either or both of these functional groups. Accordingly, 2,2-difluoro-1-(trifluoromethyl)vinyl isocyanate, for instance, is a monomer of general utility for introducing crosslinking sites in vinyl polymers.

PROCESS

A preferred process for making the vinyl isocyanates of this invention comprises reacting a polyfluoroalkyl imine of the formula

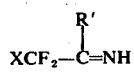

with oxalyl chloride at a temperature between about 0°C. to 150°C, hereby forming an intermediate isocyanate of the formula

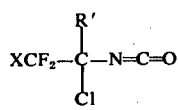

wherein:

R' is lower perfluoroalkyl, lower ω-chloroperfluoroalkyl or lower ω-hydroperfluoroalkyl, and X is fluorine or chlorine, and reacting said isocyanate with zinc metal in the absence of oxalyl chloride.

In a typical process for making the novel intermediate secondary isocyanates of this invention by reacting the appropriate imine with oxalyl chloride, it is preferred to operate the reaction in the absence of any solvent or diluent. However, solvents can be employed if desired. If employed, the solvents should not react with the reactants or with the products of the invention. Operable inert solvents include methylene chloride, ether, and the like. Catalysts although not necessary, can be employed and such catalysts are basic compounds such as pyridine, triethylamine, tributylamine, etc. Imine starting reactants are disclosed in coassigned U.S. Pat. No. 3,226,439, W. J. Middleton. One process therein disclosed for making the imine is to react hydrazoic acid ($HN_3$) with a polyhalothioketone. Another process disclosed therein is to prepare the imine in two steps from the corresponding ketone and ammonia.

A typical process for making the novel intermediate primary isocyanates of this invention is to react the appropriate 2,3-dibromo- or 2,3-dichloro-trifluoropropionyl halide with powdered sodium azide in an inert solvent at temperatures from 0° to 50°C, and then heat the resulting solution of acyl azide to between about 80° to 130°C until evolution of nitrogen stops. Solvents useful for this process should have a boiling point above 80°C at atmospheric pressure and should be inert to acyl halides and isocyanates. Examples of useful solvents are aromatic hydrocarbons such as toluene and xylene, ethers such as diethylene glycol dimethyl ether and dibutyl ether, and substituted aromatic hydrocarbons such as chlorobenzene and benzonitrile.

The novel intermediate isocyanates of this invention, after formation, are isolated by distillation and reacted with powdered zinc metal in the presence of a solvent or diluent such as ether, tetrahydrofuran, diethylene glycol dimethyl ether or the like. Although not particularly critical, temperature should generally be maintained between about 0° to 100°C. Zinc metal should not be added to the isocyanates when oxalyl chloride is present. If all or substantially all of the oxalyl chloride is consumed in the formation of the intermediate isocyanate, then there is no need for distillation before addition of the zinc.

DESCRIPTION OF THE PREFERRED EMBODIMENTS

The following Examples are meant to illustrate but not to limit the invention. Temperatures are in degrees Centigrade unless otherwise noted. The fluorine nmr spectra were obtained with a high resolution spectrometer operating at 56.4 MHz. Peak center positions are reported in parts per million (ppm) higher field displacement from the $^{19}F$ resonance of $CCl_3F$ used as an internal standard.

EXAMPLE 1

1,2-dichloro-2,2-difluoro-1-(trifluoromethyl)ethyl isocyanate

A mixture of 465 g (2.5 moles) of chloropentafluoroacetone imine, 381 g (2.5 moles) of oxalyl chloride, and 2.5 ml of pyridine was refluxed for 3 days. Distillation gave 315 g (52% conversion) of 1,2-dichloro-2,2-difluoro-1-(trifluoromethyl)ethyl isocyanate as a colorless liquid: bp 85-85.5°; $n_D^{25}$ 1.3580; ir (liquid) 4.42 μ (NCO); $^{19}F$ nmr ($CCl_3F$) δ 62.9 ppm (q, J = 24 Hz, 2F) and δ 75.7 ppm (t, J = 24 Hz, 3F).

Anal. Calc'd. for $C_4Cl_2F_5NO$: C, 19.69; Cl, 29.07; F, 38.94; N, 5.75. Found: C, 19.39; Cl, 28.81; F, 38.76; N, 5.67.

EXAMPLE 2

2,2-difluoro-1-(trifluoromethyl)-vinyl isocyanate

A 244 g sample (1.0 mole) of 1,2-dichloro-2,2-difluoro-1-(trifluoromethyl)ethyl isocyanate was added dropwise to a stirred suspension of 98 g (1.5 gram atom) of powdered zinc in 1000 ml of glycol dimethyl ether at such a rate that the temperature warmed to 45° and remained between 45°–50°. The reaction mixture was stirred for 1 hr after the addition, and then the most volatile portion was distilled under reduced pressure (5 mm) into a trap cooled oled to −78 °. The condensate in the trap was redistilled to give 158 g (91%) of 2,2-difluoro-1-(trifluoromethyl)vinyl isocyanate as a colorless liquid: bp 42.3–42.5°, ir (liquid), 4.38 $\mu$ (NCO) and 5.67 $\mu$ (=CF$_2$); $^{19}$F nmr (CCl$_3$F) $\delta$ 66.6 ppm (d, J = 9 Hz to d, J = 23 Hz, 3F) $\delta$ 82.9 ppm (d, J = 21 Hz to q, J = 9 Hz, IF) and $\delta$ 89.7 ppm (d, J = 21 Hz to d, J = 23 Hz, IF).

Anal. Calc'd. for C$_4$F$_5$NO: C, 27.76; F, 54.90; N, 8.10. Found: C, 27.70; F, 54.46; N, 7.74.

EXAMPLE 3

2,2-Difluoro-1-(trifluoromethyl)vinyl Isocyanate Homopolymer

An 8.7 g sample of 2,2-difluoro-1-(trifluoromethyl-vinyl isocyanate, as made in Example 2, was added dropwise to a suspension of 0.5 g cesium fluoride in 25 ml of anhydrous acetonitrile cooled to 0°. The reaction mixture was stirred at 25° for 18 hr, and then filtered and evaporated to dryness. There was obtained 8.1 g of a light-orange powder, soluble in acetone. The ir spectrum showed a strong band at 5.70$\mu$, but no band for NCO at ca 4.4$\mu$.

Anal. Calc'd for C$_4$F$_5$NO: C, 27.76; F, 54.90; N, 8.10. Found: C, 26.19; H, 0.14; F, 53.52; N, 7.97.

EXAMPLE 4

Copolymer of Tetrafluoroethylene with 2,2-Difluoro-1-(trifluoromethyl)vinyl Isocyanate 2,2-Difluoro-1-(trifluoromethyl)vinyl isocyanate, 3.26 g (20 mmoles), and 2.00 g (20 mmoles) of tetrafluoroethylene were distilled into a platinum tube. The latter had been prepared from a 10 inch piece of ¾ inch tubing; its lower end was sealed shut and its upper end connected to a vacuum manifold with a vacuum tight seal. 1,1,1-trichlorotrifluoroethane, 9 ml, and 48 mg (0.36 mmole) of perfluoropropionyl peroxide initiator in 0.5 ml of the same solvent were added with syringes. The tube was sealed with a torch under vacuum and heated to 60° at 3000 atms for 16 hrs. After opening, the solid product was dried at 100° to give 1.19 g (23%) of gray polymer that was milled to powder.

The product had infrared bands characteristic of isocyanate and of tetrafluoroethylene polymer, and contained 1.82% nitrogen, corresponding to 21 weight % of isocyanate. Extraction with boiling acetone resulted in only 3% weight reduction. Differential thermal analysis showed a transition at 248° consistent with the tetrafluoroethylene copolymer structure.

EXAMPLE 5

1-Chloro-1-(trifluoromethyl)pentafluoropropyl isocyanate

By the procedure of Example 1, perfluorobutyliden-2-imine, oxalyl chloride and pyridine will yield 1-chloro-1-(trifluoromethyl)pentafluoropropyl isocyanate.

EXAMPLE 6

2,2-Difluoro-1-(pentafluoroethyl)vinyl isocyanate

By the procedure of Example 2, adding 1-chloro-1-(trifluoromethyl)pentafluoropropyl isocyanate to a suspension of powdered zinc in ether will yield 2,2-difluoro-1-(pentafluoroethyl)vinyl isocyanate.

EXAMPLE 7

1,3-dichloro-1-(trifluoromethyl)tetrafluoropropyl isocyanate

By the procedure of Example 1, 1-chloroheptafluorobutyliden-3-imine, oxalyl chloride and pyridine will yield 1,3-dichloro-1-(trifluoromethyl)tetrafluoropropyl isocyanate.

EXAMPLE 8

2,2-Difluoro-1-(2-chlorotetrafluoroethyl)vinyl isocyanate

By the procedure of Example 2, adding 1,3-dichloro-1-(trifluoromethyl)tetrafluoropropyl isocyanate to a suspension of powdered zinc in ether will yield 2,2-difluoro-1-(2-chlorotetrafluoroethyl)vinyl isocyanate.

EXAMPLE 9

1-Chloro-3H-1-(trifluoromethyl)tetrafluoropropyl isocyanate

By the procedure of Example 1, 1H-heptafluorobutyliden-3-imine, oxalyl chloride and pyridine will yield 1-chloro-3H-1-(trifluoromethyl)tetrafluoropropyl isocyanate.

EXAMPLE 10

2,2-Difluoro-1-(2H-tetrafluoroethyl)vinyl isocyanate

By the procedure of Example 2, adding 1-chloro-3H-1-(trifluoromethyl)tetrafluoropropyl isocyanate to a suspension of powdered zinc in ether will yield 2,2-difluoro-1-(2H-tetrafluoroethyl)vinyl isocyanate.

EXAMPLE 11

2-Chloro-1,1,2,2-tetrafluoroethyl isocyanate and 1,2-dichloro-1,2,2-trifluoroethyl isocyanate.

A 40-g sample (0.2 mole) of 2,3-dichloro-2,3,3-trifluoropropionyl fluoride was added dropwise to a stirred suspension of 14.3 g (0.22 mole) of powdered sodium azide in 200 ml of xylene. The reaction mixture was stirred for 18 hours at 25° and then warmed slowly to 110°. When the evolution of nitrogen ceased, the volatile portion of the reaction mixture was distilled to give 10.14 g (29%) of 2-chloro-1,1,2,2-tetrafluoroethyl isocyanate as a colorless liquid: bp 31°–31.5°; n$_D$$^{25}$ 1.3122; $^{19}$F nmr (CCl$_3$F) $\delta$ 73.1 ppm (t, J = 4 Hz, 2F) and 83.6 ppm (broad t, 2F); and 3.03 g (8%) of 1,2-dichloro-1,2,2-trifluoroethyl isocyanate as a colorless liquid: bp 67°–68°; n$_D$$^{25}$ 1.3650; $^{19}$F nmr (CCl$_3$F) $\delta$ 69.9 ppm (q, 2F) and 77.9 ppm (broad t, 1F).

Anal. Calcd for C$_3$ClF$_4$NO: C, 20.30; Cl, 19.98; F, 42.82; N, 7.89 Found: C, 20.69; Cl, 20.23; F, 43.11; N, 7.59

Anal. Calcd for $C_3Cl_2F_3NO$: C, 18.58; Cl, 36.56; F, 29.39; N, 7.22 Found: C, 19.01; Cl, 36.19; F, 29.52; N, 6.96

Preparation of the 2,3-Dichloro-2,3,3-trifluoropropionyl fluoride

Chlorine, 60 ml measured at $-78°$ (ca 93 g, 1.31 mole) was slowly distilled into a "Pyrex" flask containing 100 ml (ca 168 g, 1.31 mole) of trifluoroacrylyl fluoride that was being irradiated with a 275 watt sun lamp at a 6 inch distance. The temperature was kept between $0°-20°$, and the addition required 6 hrs. Distillation of the reaction mixture gave 187.65 g (72%) of 2,3-dichloro-2,3,3-trifluoropropionyl fluoride as a colorless liquid: bp $49°-50°$; $n_D^{25}$ 1.3294; ir (liquid) 5.35 $\mu$ (COF); $^{19}F$ nmr ($CCl_3F$) δ-21.7 ppm (d, J = 15 Hz to d, J = 10.3 Hz, J = 10.3 Hz, 1F) 64.7 ppm (d, J = 173 Hz to d, J = 10.3 Hz to d, J = 8.6 Hz, 1F), 68.8 (d, J = 173 Hz to d, J = 10.3 Hz to d, J = 10.3 Hz, 1F) and 123.7 ppm (d, J = 15 Hz to d, J = 10.3 Hz to d, J = 8.6 Hz, 1F).

Anal. Calcd for $C_3Cl_2F_4O$: C, 18.11; Cl, 35.65; F, 38.20 Found: C, 18.20; Cl, 34.87; F, 38.33

EXAMPLE 12

Trifluorovinyl isocyanate $$CF_2ClCFCl-NCO + Zn \rightarrow CF_2=CF-NCO + ZnCl_2$$

A 35.2-g sample (0.18 mole) of 1,2-dichloro-1,2,2-trifluoroethyl isocyanate, made by the procedure of Example 11, was added dropwise to a stirred suspension of 23.5 g of activated zinc dust in 100 ml of di(2-methoxyethyl) ether (Diglyme) heated to $60°$. The temperature was maintained at $60°-70°$, and stirring was continued at this temperature for 1 hr after the addition was completed. The volatile products (7.8 ml) were distilled from the reaction mixture and then redistilled to give 4 ml (at $-78°$, about 7 g, 32%) of trifluorovinyl isocyanate, bp $19°-20°$, and 1.7 g of 2-chloro-1,1,2,2-tetrafluoroethyl isocyanate, bp $31°$. The trifluorovinyl isocyanate was identified by its $^{19}F$ nmr spectrum in $CCl_3F$: δ 112.6 ppm (d, J = 85 Hz to d, J = 50 Hz, 1F), δ 123.0 ppm (d, J = 121 Hz to d, J = 85 Hz, 1F) and δ 145.4 ppm (d, J = 121 Hz to d, J = 50 Hz, 1F).

EXAMPLE 13

1,2-Dichloro-1,2,2-trifluoroethyl isocyanate

A 65-g sample (0.3 mole) of 2,3-dichloro-2,3,3-trifluoropropionyl chloride was added dropwise to a stirred suspension of 21.67 g (0.33 mole) of powdered sodium azide in 300 ml of dry xylene. The reaction mixture was stirred at $25°$ for 20 hrs, and then slowly warmed to $112°$ over a period of 6 hrs. The material boiling below xylene was distilled from the reaction mixture, and then redistilled to give 32.18 g (62% yield, 55% conversion) of 1,2-dichloro-1,2,2-trifluoroethyl isocyanate as a colorless liquid: bp $68°-69°$; $n_D^{25}$ 1.3654; ir (liquid) 4.40$\mu$ (NCO); and 7.8 g of recovered 2,3-dichloro-2,3,3-trifluoropropionyl chloride.

Anal. Calcd for $C_3Cl_2F_3NO$: C, 18.58; Cl, 36.56; F, 29.39; N, 7.22 Found: C, 18.86; Cl, 36.97; F, 28.92; N. 7.32.

Preparation of the 2,3-dichloro-2,3,3-trifluoroprionyl chloride

A 100-g sample (0.5 mole) of 2,3-dichloro-2,3,3-trifluoropropionyl fluoride, prepared as shown in Example 11, was added dropwise to a stirred suspension of 34 g (0.25 mole) of aluminum chloride in 200 ml of methylene chloride. The reaction mixture was stirred for two hrs, and the volatile portion was distilled under reduced pressure into a Dry-ice cooled trap. Redistillation gave 70.6 g (66%) of 2,3-dichloro-2,3,3-trifluoropropionyl chloride as a colorless liquid: bp $87.5°-88°$; $n_d^{25}$ 1.3812; ir (liquid 5.57$\mu$ (C=O); $^{19}F$ nmr ($CCl_3F$) δ 64.2 ppm (d, J = 173 Hz to d, J = 8 Hz, 1F), 65.7 ppm (d, J = 173 Hz to d, J = Hz, 1F) and 117.4 ppm (d, J = 10 Hz to d, J = 8 Hz, 1F).

Anal. Calcd. for $C_3Cl_3F_3O$: C, 16.73; Cl, 49.38; F, 26.46 Found: C, 16.87; Cl, 49.07; F, 26.56.

EXAMPLE 14

1,2-Dibromo-1,2,2-trifluoroethyl isocyanate and 2-bromo-1-chloro-1,2,-2-trifluoroethyl isocyanate

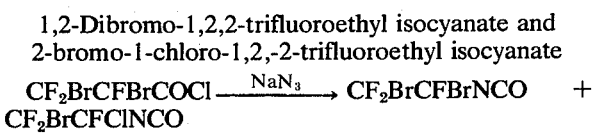

A 27.4-g sample (0.09 mole) of 2,3-dibromo-2,3,3-trifluoropropionyl chloride was added dropwise to a stirred suspension of 6.5 g (0.1 mole) of powdered sodium azide in 100 ml xylene. The reaction mixture was stirred for several hours at $25°$, and then heated gently to relfux until nitrogen evolution ceased. The most volatile portion was distilled out of the reaction mixture and then redistilled to give 2.5 g (12%) of 2-bromo-1-chloro-1,2,2-trifluoroethyl isocyanate as a colorless liquid: bp $89°-91°$; ir (liquid) 4.43 $\mu$ (NCO); $^{19}F$ nmr ($CCl_3F$) δ 63.8 ppm (d, J = 10 Hz, 2F) and 75.7 ppm (broat t, J = 10 Hz, 1F); and 6.7 g (26%) of 1,2-dibromo-1,2,2-trifluoroethyl isocyanate as a colorless liquid: bp $107°-110°$; ir (liquid) 4.43 $\mu$ (NCO); $^{19}F$ nmr ($CCl_3F$) δ 61.3 ppm (d to d, 2F) and δ 71.7 ppm (broad t, 1F).

Anal. Calcd for $C_3BrClF_3NO$: C, 15.11; Br, 33.52; Cl, 14.88; F, 23.91; N, 5.87

Found: C, 15.50; Br, 33.60; Cl, 15.01; F, 24.14; N, 5.99

Anal. Calcd for $C_3Br_2F_3NO$: C, 12.74; Br, 56.50; F, 20.15; N, 4.96 Found: C, 13.10; Br, 57.00; F, 20.17; N, 5.30

Preparation of 2,3-Dibromo-2,3,3-trifluoropropionyl chloride

A 163-g (0.56 mole) sample of 2,3-dibromo-2,3,3-trifluoropropionyl fluoride was added dropwise to a mechanically stirred suspension of 76 g (0.56 mole) of aluminum chloride in 282 ml of methylene chloride. The reaction mixture warmed spontaneously to $40°$. After cooling, the volatile portion of the reaction mixture was distilled under reduced pressure into a Dry Ice-cooled trap. Redistillation gave 97.5 g (57%) of 2,3-dibromo-2,3,3-trifluoropropionyl chloride as a colorless liquid: bp $128°-129°$; $n_D^{25}$ 1.4436; ir (liquid) 5.57 $\mu$ (COCl); $^{19}F$ nmr ($CCl_3F$) δ 55.7 ppm (d, J = 175 Hz to d, J = 14.5 Hz, 1F), 57.9 ppm (d, J = 175 Hz to d, J = 16 Hz, 1F) and 116.5 ppm (d, J = 16 Hz to d, J = 14.5 Hz, 1F).

Anal. Calcd for $C_3Br_2ClF_3O$: C, 11.84; Br, 52.52; Cl, 11.65; F, 18.73 Found: C, 12.09; Br, 52.32; Cl, 11.55; F, 18.99

Preparation of 2,3-dibromo-2,3,3-trifluoropropionyl fluoride

A 128-g sample (1 mole) of trifluoroacrylyl fluoride was slowly distilled into 160 g (1 mole) of bromine cooled to 0°. The reaction mixture was stirred for 3 days at room temperature and then distilled to give 260.85 g (93%) of 2,3-dibromo-2,3,3-trifluoropropionyl fluoride as a colorless liquid: bp 88°–89°; $n_D^{25}$ 1.3938; ir (liquid) 5.33 μ (COF); 19F nmr ($CCl_3F$) δ-21.3 ppm (d, J = 11.0 Hz to d, 13.3 Hz to d, 14.3 Hz, 1F), 56.3 ppm (d, 177 to d, 15.2, to d, 14.3, 1F), 60.9 ppm (d, 177 to d, 16.8 to d, 11.0) and 125.4 ppm (d, 16.8 to d, 15.2 to d, 13.3).

Anal. Calcd for $C_3Br_2F_4O$: C, 12.52; Br, 55.52; F, 26.40 Found: C, 12.75; Br, 55.32; F, 26.69

EXAMPLE 15

Trifluorovinyl isocyanate

A solution in 10 ml of Diglyme of 5.66 g (0.02 mole) of 1,2-dibromo-1,2,2-trifluoroethyl isocyanate, made as shown in Example 14, was added dropwise to a stirred suspension of 2.6 g (0.04 mole) of zinc dust and 0.1 g zinc chloride in 25 ml of Diglyme. The reaction mixture became warm. The most volatile portion was distilled out under reduced pressure (5 mm Hg) into a Dry Ice-cooled trap and the condensate in the trap was redistilled to give 1.2 ml (2.0 g, 81%) of trifluorovinyl isocyanate. (Identified by $^{19}F$ nmr).

EXAMPLE 16

2-Bromo-1,1,2,2-tetrafluoroethyl isocyanate

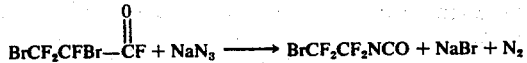

A 25-g sample (0.087 mole) of 2,3-dibromo-2,3,3-trifluoropropionyl fluoride, prepared as shown in Example 14, was added dropwise to a stirred suspension of 6.5 ml of xylene. The mixture was stirred for several hours at about 25°, and then heated gently to about 110° until no further evolution of nitrogen occurred. The most volatile portion was distilled out of the reaction mixture and then redistilled to give 8.35 g (43%) of 2-bromo-1,1,2,2-tetrafluoroethyl isocyanate as a colorless liquid: bp 50°; ir (liquid) 4.40μ (NCO); $^{19}F$ nmr ($CCl_3F$) δ 68.0 ppm (t, J = 5 cps, 2F) and 79.3 ppm (broad t, J = 5 cps, 2F).

Anal. Calcd for $C_3BrF_4NO$: C, 16.23; Br, 36.01; F, 34.24; N, 6.13 Found: C, 16.37; Br, 35.61; F, 34.79; N, 6.39.

EXAMPLE 17

Trifluorovinyl Isocyanate

A solution in 20 ml Diglyme of 19.0 g (0.085 mole) of 2-bromo-1,1,2,2-tetrafluoroethyl isocyanate, prepared as shown in Example 16, was added dropwise to a suspension of 13 g (0.2 mole) of zinc dust and 0.1 g zinc chloride in 100 ml Diglyme heated to 80°. The reaction temperature was maintained at 80°–90° during the addition, and then the most volatile portion was distilled from the reaction mixture and redistilled to give 2.1 ml (ca 3.6 g, 29%) of a colorless liquid, bp 18°–21°. The $^{19}F$ nmr spectrum indicated the product was 90% trifluorovinyl isocyanate.

EXAMPLE 18

1-Chloro-2,2,2-trifluoro-1-(trifluoromethyl)ethyl isocyanate

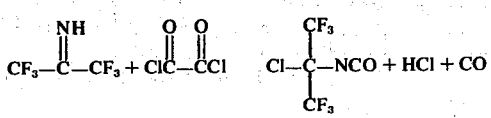

A mixture of 127 g (1 mole) of oxalyl chloride, 165 g (1 mole) of perfluoropropyliden-2-imine, and 5 ml of pyridine was heated in a 600 ml Hastelloy tube at 100° for 4 hrs, 105° for 4 hrs, and 200° for 4 hrs. The bomb was cooled and vented, and the contents were filtered to remove suspended solid. Distillation gave 102.3 g of a 25:75 mixture of $(CF_3)_2CClNH_2$ and the isocyanate, bp 46.0°–46.5°, and 29.3 g of pure isocyanate as a colorless liquid: bp 50.5°–51.0°; $^{19}F$ nmr ($CCl_3F$) ε 78.0 (s); ir (liquid) 4.40 μ.

Anal. Calcd for $C_4ClF_6NO$: C, 21.12; Cl, 15.58; F, 50.11; N, 6.16 Found C, 21.11; Cl, 6.01; F, 49.52; N, 6.16

EXAMPLE 19

2,2-Difluoro-1-(trifluoromethyl)vinyl isocyanate

Dehalogenation (one Cl and one F) according to the procedure of Example 2 of 1-chloro-2,2,2-trifluoro-1-(trifluoromethyl)-ethyl isocyanate will yield 2,2-difluoro-1-(trifluoromethyl)-vinyl isocyanate.

EXAMPLE 20

1,2-Dichloro-2,2-difluoro-1-(chlorodifluoromethyl)ethyl Isocyanate $$CF_2Cl-\overset{NH}{\underset{}{C}}-CF_2Cl + Cl-\overset{O}{\underset{}{C}}-\overset{O}{\underset{}{C}}-Cl \rightarrow Cl-\underset{CF_2Cl}{\overset{CF_2Cl}{C}}-NCO + CO + HCl$$

A mixture of 39.6 g (0.2 mole) of 1,3-dichloro-1,1,3,3,-tetrafluoro-propyliden-2-imine and 31.8 g (0.25 mole) of oxalyl chloride was refluxed for 5 days. Distillation of the reaction mixture gave 33.5 g (64%) of 1,2-dichloro-2,2-difluoro-1-(chlorodifluoromethyl)ethyl isocyanate as a colorless liquid: bp 121.5°–122°; $n_D^{25}$ 1.3953; ir (liquid) 4.39 μ (NCO); $^{19}F$ nmr ($CCl_3F$) δ 60.9 ppm (s).

Anal. Calcd for $C_4Cl_3F_4NO$: C, 18.45; Cl, 40.85; F, 29.18; N, 5.38 Found: C, 18.50; Cl, 40.61; F, 29.22; N, 5.69

EXAMPLE 21

2,2-Difluoro-1-(chlorodifluoromethyl)vinyl isocyanate

Dechlorination according to the procedure of Example 2 of 1,2-dichloro-2,2-difluoro-1-(chlorodifluoromethyl)ethyl isocyanate will yield 2,2-difluoro-1-(chlorodifluoromethyl)vinyl isocyanate.

EXAMPLE 22

Poly(Trifluorovinyl isocyanate): Spontaneous Polymerization

A sample of trifluorovinyl isocyanate sealed in a glass tube was allowed to remain at room temperature (ca 25°) for 17 days. The tube was broken open, and the polymer was removed as a clear, colorless, flexible rod, mp > 250°.

Anal. Calcd for $(C_3F_3NO)_n$: C, 29.29; F, 46.33; N, 11.38 Found: C, 29.07; F, 45.55; N, 10.75

The polymerization can be inhibited and the monomer can be stored at room temperature if small amounts of conventional radical inhibitors such as D-limonene or 2-trifluoromethylphenothiazine are added to the liquid monomer.

EXAMPLE 23

Poly(Trifluorovinyl Isocyanate): Bulk Polymerization

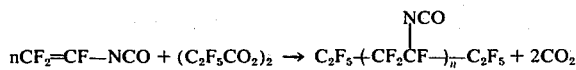

A 10% solution of perfluoropropionyl peroxide in 1,1,1-trichlorotrifluoroethane, 50 $\mu$l, was injected into a glass tube containing 3.0 g of trifluorovinyl isocyanate cooled to $-78°$. The tube was sealed and then allowed to warm to room temperature. Polymerization was complete in about one hr. The tube was opened, and the colorless polymer was removed. A thin stiff film was pressed from this polymer at 150°C and 15,000 lbs/in². The film showed an ir absorption at 4.42 $\mu$, indicating the presence of isocyanate groups. Films pressed at higher temperatures (about 350°) were stiffer and more brittle, and showed a weaker isocyanate band in the infrared spectrum, indicating that cross-linking is occurring at elevated temperatures.

Anal. Calcd for $(C_3F_3NO)_n$: F, 46.30; N, 11.38 Found: F, 45.02; N, 10.90.

EXAMPLE 24

Poly(Trifluorovinyl Isocyanate): Solution Polymerization

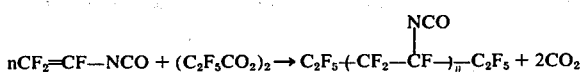

A 10% solution of perfluoropropionyl peroxide in 1,1,1-trichlorotrifluoroethane, 50 $\mu$l, was injected into a flask fitted with a serum cap and containing a solution of 2.0 g trifluorovinyl isocyanate in 25 ml of 1,1,1-trichlorotrifluoroethane at 25°. After standing at room temperature for 2 days, the contents of the flask contained a mixture of precipitated polymer curds and a solution of the polymer. The solvent was removed by evaporation under reduced pressure to give 2.0 g of rubbery polymer.

EXAMPLE 25

Copolymer of Perfluoro(2-methylene-4-methyl-1,3-dioxolane) and Trifluorovinyl Isocyanate An 80 ml stainless steel reactor containing 12.2 g (50 mmoles) of perfluoro(2-methylene-4-methyl-1,3-dioxolane), 5 mg of $\alpha,\alpha'$-azodiisobutyronitrile and 40 ml of 1,1,1-trichlorotrifluoroethane was cooled to about $-75°C$ and successively flushed with nitrogen and evacuated several times. After final evacuation, 2.5 g (2. mmoles) of trifluorovinyl isocyanate was introduced from an interconnected supply cylinder. The reactor was then closed and heated 16 hours at 100° in a rocker assembly.

The polymeric product was isolated by evaporating the solvent from the clear, colorless reaction mixture and heating the residue at 125°. The dry polymer had an inherent viscosity of 0.21 ($n_{inh}$, 25°, 0.1% in 1,1,1-trichlorotrifluoroethane), contained nitrogen (N: 2.02, 1.98), and showed strong infrared absorption at 4.4$\mu$ (isocyanate group). It formed slightly hazy films when pressed at 150°/5000 psi.

EXAMPLE 26

Terpolymer of Perfluoro(2-methylene-4-methyl-1,3-dioxolane), vinylidene fluoride and trifluorovinyl isocyanate Following the procedure of Example 25, 9.8 g (40 mmoles) of perfluoro(2-methylene-4-methyl-1,3-dioxolane), 1.1 g (17 mmoles) of vinylidene fluoride and 1.2 g (10 mmoles) of trifluorovinyl isocyanate dissolved in 50 ml of 1,1,1-trichlorotrifluoroethane were heated at 100°C for 16 hours in the presence of 5 mg of $\alpha,\alpha'$-azodiisobutyronitrile. The polymeric product weighed 4.2 g, had an inherent viscosity of 0.24 ($n_{inh}$, 25°, 0.1% in 1,1,1-trichlorotrifluoroethane), analysed for 1.40% nitrogen, and showed the presence of $-NCO$ and $-CH_2-$ by infrared analysis.

EXAMPLE 27

Terpolymer of Perfluoro(2-methylene-4-methyl-1,3-dioxolane), vinylidene fluoride and 2,2-difluoro-1-(trifluoromethyl)vinyl isocyanate Following the procedure of Example 26, a terpolymr was prepared from 12.2 g (50 mmoles) of perfluoro(2-methylene-4-methyl-1,3-dioxolane), 1.1 g (17 mmoles) of vinylidene fluoride and 2.94 g (17 mmoles) of 2,2-difluoro-1-(trifluoromethyl)vinyl isocyanate dissolved in 100 ml of 1,1,1-trichlorotrifluoroethane with 5 mg of $\alpha,\alpha'$-azodiisobutyronitrile as initiator. The product weighing 1.39 g had an inherent viscosity of 0.23 ($\eta_{inh}$, 25°C., 0.1% in 1,1,1-trichlorotrifluoroethane), contained 0.5% nitrogen, and showed the presence of $-NCO$ and $-Ch_2-$ by infrared analysis. The polymer produced a clear film on heating at 150°C. under atmospheric pressure.

UTILITY

The utility of the novel dichloro isocyanates lies in making the novel vinyl isocyanate monomers with ultimate utility based, inter alia, on the use of vinyl isocyanate homopolymers and copolymers in water-proofing and oil-proofing both cloth and paper materials; and in the use of vinyl isocyanate copolymers in the form of films for wrapping, wire insulation and the like. It is expected that the films would be nonflammable in that they would not burn spontaneously or support combustion and film use could be most desirable for applications in which such nonflammability is important.

Uses of a representative homopolymer and of a representative copolymer in the treatment of cloth and paper, respectively, are shown below. Examples 25 and 27 show the formation of copolymer films. Example 23 shows formation of self-supporting poly(trifluorovinyl isocyanate) film.

EXAMPLE A

WATER- AND OIL-PROOFING CLOTH

A 50 mg sample of the homopolymer described in Example 3 was dissolved in 5 ml of acetone, and a 6 × 3 cm piece of cotton fabric was treated by saturation with the resulting solution and then dried in air. Drops of mineral oil and of water placed separately on the fabric did not penetrate. Drops of oil and water placed on untreated but otherwise similar piece of cloth were absorbed immediately.

EXAMPLE B

WATER- AND OIL-PROOFING PAPER

A 100 mg sample of the copolymer described in Example 4 was mixed with 10 ml of chlorotrifluoromethane, and the resulting mixture was ground in a mortar until a fine suspension was obtained. The suspension was applied to a piece of filter paper 5.5 cm in diameter. The treated paper was dried in air and then put in a press and heated at 200° at 10,000 lbs/sq. in. for 5 min. Drops of water and of mineral oil placed separately on the treated paper did not penetrate in 5 min. time. Drops of water and oil placed on a piece of untreated paper penetrated immediately.

Although the invention has been described and exemplified by way of specific embodiments, it is not intended that it be limited thereto. As will be apparent to those skilled in the art, numerous modifications and variations of these embodiments can be made without departing from the spirit of the invention or the scope of the following claims.

The embodiments of the invention in which an exclusive property or privilege is claimed are defined as follows:

1. A homopolymer of a vinyl isocyanate of the formula

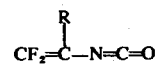

wherein:
R is fluorine, lower perfluoroalkyl, lower ω-chloroperfluoroalkyl or lower ω-hydroperfluoroalkyl.

2. A homopolymer of claim 1 in which the vinyl isocyanate is 2,2-difluoro-1-(trifluoromethyl)vinyl isocyanate.

3. A homopolymer of claim 1 in which the vinyl isocyanate is trifluorovinyl isocyanate.

* * * * *

UNITED STATES PATENT OFFICE
CERTIFICATE OF CORRECTION

PATENT NO. : 3,965,074
DATED : June 22, 1976
INVENTOR(S) : William J. Middleton

Page 1 of 2

It is certified that error appears in the above-identified patent and that said Letters Patent are hereby corrected as shown below:

Column 4, line 67, "5.75" should read -- 5.74 --.

Column 5, line 13, delete "oled".

Column 5, line 27, "(trifluoromethyl-" should read -- (trifluoromethyl)- --.

Column 8, line 1, "trifluoprionyl" should read -- trifluoropropionyl --.

Column 8, line 15, "J = Hz" should read -- J = 10 Hz --.

Column 8, line 37, "broat" should read -- broad --.

Column 9, line 42, after "6.5" add -- g (0.1 mole) of powdered sodium azide in 100 --.

Column 10, line 7, there should be a forward arrow (yields sign) between the two formulae.

Column 10, line 20, "$\epsilon$" should read -- $\delta$ --.

Column 12, line 34, "terpolymr" should read -- terpolymer --.

UNITED STATES PATENT OFFICE

CERTIFICATE OF CORRECTION

Patent No. 3,965,074   Dated June 22, 1976

Inventor(s) William J. Middleton

It is certified that error appears in the above-identified patent and that said Letters Patent are hereby corrected as shown below:

Column 12, line 45, "-Ch$_2$-" should read --- -CH$_2$- ---.

Signed and Sealed this

Thirty-first Day of October 1978

[SEAL]

Attest:

RUTH C. MASON
Attesting Officer

DONALD W. BANNER
Commissioner of Patents and Trademarks